(12) United States Patent
Guezennec et al.

(10) Patent No.: US 7,015,206 B2
(45) Date of Patent: Mar. 21, 2006

(54) **USE OF A POLYSACCHARIDE EXCRETED BY THE *VIBRIO DIABOLICUS* SPECIES IN BONE REPAIR**

(75) Inventors: Jean Guezennec, Plouzane (FR); Philippe Zanchetta, Brest (FR)

(73) Assignee: Institut Francais de le Recherche pour l'Exploitation de la Mer, Issey les Moulineaux (FR)

( * ) Notice: Subject to any disclaimer, the term of this patent is extended or adjusted under 35 U.S.C. 154(b) by 0 days.

(21) Appl. No.: 10/312,886

(22) PCT Filed: Jul. 4, 2001

(86) PCT No.: PCT/FR01/02139

§ 371 (c)(1), (2), (4) Date: Aug. 5, 2003

(87) PCT Pub. No.: WO02/02051

PCT Pub. Date: Jan. 10, 2002

(65) Prior Publication Data

US 2004/0030403 A1   Feb. 12, 2004

(30) Foreign Application Priority Data

Jul. 4, 2000   (FR) ................................. 00 08676

(51) Int. Cl.
*A61K 31/70* (2006.01)
*A61F 2/28* (2006.01)

(52) U.S. Cl. ................. 514/54; 514/61; 538/123; 538/123.1; 538/114; 435/101; 435/104; 435/41; 435/72; 623/23.57; 623/23.59

(58) Field of Classification Search ............... 514/54, 514/61; 536/123, 123.1, 114; 435/101, 435/104, 41, 72; 623/23.57, 23.59
See application file for complete search history.

(56) References Cited

U.S. PATENT DOCUMENTS 6,436,680 B1 *   8/2002   Guezennec et al. ......... 435/101
6,642,285 B1 *  11/2003   Bohner ....................... 523/115

FOREIGN PATENT DOCUMENTS

WO         98 38327          9/1998

OTHER PUBLICATIONS

Helene Rougeaux et al.: "Structure of the exopolysaccharide of *Vibrio diabolicus* isolated from a deep-sea hydrothermal vent" Carbohydrate Research, vol. 322, no. 1-2, pp. 40-45, Nov. 23, 1999.
M. Loaec et al.: "Chelating properties of bacterial exoplysaccharides from deep-sea hydrothermal vents" Carbohydrate Polymers vol. 35, no. 1-2, pp. 65-70, Jan. 1998.
G. Raguenes et al.: "*Vibrio diabolicaus* sp. nov., a new polysaccharide-secreting organism isolated from a deep-sea hydrothermal vent polychaete annelid, alvinella pompejana" International Journal of Systematic Bacteriology, vol. 47, no. 4, pp. 989-995 Oct. 1, 1997.

* cited by examiner

*Primary Examiner*—James O. Wilson
*Assistant Examiner*—Devesh Khare
(74) *Attorney, Agent, or Firm*—Young & Thompson

(57) ABSTRACT

The invention concerns the use of a polysaccharide excreted by the *Vibrio diabolicus* species for making a medicine with cicatrising activity, in particular bone repair activity. The invention also concerns a bone reconstruction biomaterial comprising said polysaccharide and a bone endoprosthesis whereof the surface is coated with such a polysaccharide.

10 Claims, No Drawings

USE OF A POLYSACCHARIDE EXCRETED BY THE *VIBRIO DIABOLICUS* SPECIES IN BONE REPAIR

The present invention relates to the use of a polysaccharide excreted by the *Vibrio diabolicus* species for producing a medicinal product with cicatrizing activity, and also to a bone reconstruction biomaterial comprising this polysaccharide.

Bone substance losses are disabling and are slow to repair. When the bone loss exceeds a critical size, no spontaneous repair can occur (J. P. Schmitz et al., *Acta Anat.*, 1990, 138, 185–192). Bone-filling materials, which conduct or induce repair, must then be used in order to restore continuity between the two sides of the bone loss.

The most long-standing transplantation techniques consist in using complete bone, which inherently comprises proteins capable of initiating and promoting the biological mechanisms of bone reconstruction, such as BMPs or bone morphogenetic proteins, osteocalcin, osteopontin and osteogenin. Autografts have the advantage of being completely tolerated by the immune system. However, the bone store is limited in an individual and the additional surgical intervention which ensues therefrom leads to risks of complications. As regards allografts or xenografts, they present risks of pathogenic agent transmission and may lead to rejection phenomena.

Due to the inadequacies of bone grafts, research has been directed toward bone substitute materials. These filling materials may be osteoinductive or osteoconductive materials.

Osteoinductive materials enable regeneration of the tissue loss according to a mechanism of cell activation by the proteins or peptides of the filler material. They are capable of inducing ossification at an ectopic site, i.e. extra-osseous ossification. By way of examples of osteoinductive substances and materials other than bone in its natural form, mention may be made of:
  growth factors and hormones (in particular cytokines, IGFs or insulin-like growth factors, and FGFs or fibroblast growth factors) for which it has been demonstrated that they promote bone reconstruction (P. A. Hill et al., *Endocrinology*, 1995, 136(1), 124–131: P. Cuevas et al., *Surg. Neurol.*, 1997, 47, 242–246; G. L. Barnes et al., *Journal of Bone and Mineral Research*, 1999, 14(11), 1805–1815). M. Isobe et al. (*Journal of Biomedical Materials Research*, 1996, 32, 433–438) have in particular proposed injecting rats subcutaneously with growth factors of the BMP type, extracted from bone tissue. BMPs, and also, in general, the other growth factors and hormones, give random results, however, when they are used clinically. The systemic effect thereof, i.e. effect not limited to the site of implantation, presents risks of diffusion of BMP into the neighboring tissues of the damaged site, and of local calcification at a non-osseous site. In addition, the use of BMPs may lead to inter- or intraspecies contaminations;
  dextran derivatives bearing functional groups chosen from carboxymethyl, benzylamide, sulfate and sulfonate (called "CMDBS") and heparan sulfates, which bind the growth factors present at the lesion, protecting them from enzymatic degradation (D. Aviezer et al., *The Journal of Biological Chemistry*, 1994, 269(1), 114–121; F. Blanquaert et al., *Journal of Biomedical Materials Research*, 1999, 44, 63–72; M. L. Colombier et al., *Journal de Parodontologie et d'Implantologie Orale*, 1998, 17(4), 403–413; M. Tardieu et al., *Journal of Cellular Physiology*, 1992, 150, 194–203). These compounds nevertheless require a vector, such as collagen, in order to be used (A. Meddahi et al., *Diabetes & Metabolism*, 1996, 22, 274–278; A. Meddahi et al., *Path. Res. Pract.*, 1994, 190, 923–928). A. Meddahi et al. (1994, ibid) have demonstrated that a particular dextran derivative, called CMDBS K (comprising 83% of carboxymethyl groups, 23% of benzylamide groups and 13% of sulfonate groups), soaked in a collagen buffer, makes it possible to partially fill, after three weeks, bone defects 3 mm in diameter produced in rat calvaria. These results cannot, however, be extrapolated to critical size lesions, the reference critical diameter for such a period of time being 5 to 8 mm.

Moreover, osteoconductive materials, as their name indicates, merely conduct the repair, without inducing any bone formation per se: they serve as a support for the biological phenomena of bone repair and are intended to be resorbed after a certain amount of time, and replaced with the newly formed bone tissue. By way of examples of osteoconductive materials, mention may be made of:
  bone in all its deproteinized and/or ceramized forms, of human or bovine origin for example (F. A. Papay et al., *The Journal of Craniofacial Surgery*, 1996, 7(5), 347–351);
  synthetic or natural calcium phosphates, such as tricalcium phosphate, biphasic calcium phosphate, hydroxyapatite, or corals (F. A. Papay et al., ibid; N. B.-A. Naaman et al., *The International Journal of Oral and Maxillofacial Implants*, 1998, 13(1), 115–120; M. Trecant et al., *Clinical Materials*, 1994, 15, 233–240);
  biovitroceramics, bioglasses.

In view of the inadequacies and the disadvantages of this state of the art in terms of bone reconstruction, the inventors therefore gave themselves the aim of providing a biomaterial which can be used in bone reconstruction, and which is suitable for the reconstruction of large losses of bone substances, i.e. of defects the size of which is greater than the critical size. This biomaterial must be biocompatible, non-immunogenic and resorbable at the end of bone reconstruction.

Surprisingly, the inventors have discovered that these aims are achieved using a particular polysaccharide, namely a polysaccharide excreted by the *Vibrio diabolicus* species.

A subject of the invention is the use of a polysaccharide excreted (termed "exopolysaccharide") by the *Vibrio diabolicus* species whose strain was deposited with the CNCM (Collection nationale de Cultures de Microorganismes [National collection of cultures of microorganisms], 28 rue du Docteur Roux; 75724 Paris, France) on Oct. 17, 1995, under the number I-1629, for producing a medicinal product with cicatrizing activity.

The physicochemical characteristics and the metabolite properties of the *Vibrio diabolicus* species (isolated from the strain HE 800, belonging to the *Vibrio* genus) are described in the PCT International application in the name of IFREMER, published under the number WO 98/38327.

The medicinal product with cicatrizing activity defined above in particular has bone repair activity, for example with a view to preparing a bone repair or filling material, such as bone endoprostheses (dental prostheses and joint prostheses for example).

Particularly advantageously, the polysaccharide defined above may be used to prepare a coating for a bone endoprosthesis, or for an osteoconductive filling material. Osteoconductive filling materials or bone endoprostheses (such as dental bone endoprostheses made of titanium or joint prostheses made of titanium without orthopedic cement) coated with such a polysaccharide can in fact integrate very rapidly into the recipient bone.

A subject of the invention is also a bone endoprosthesis, characterized in that at least part of its surface is coated with the polysaccharide as defined above.

A polysaccharide which can be used in the invention is, for example, a polysaccharide which can be obtained by precipitation with ethanol from culture supernatants of said *Vibrio diabolicus* species. This polysaccharide is such that it:

does not comprise any neutral polysaccharides, has an acid saccharide content of approximately 50% by weight, has an osamine content of approximately 50% by weight, has a glucuronic-acid/N-acetylgalactosamine/N-acetylglucosamine monosaccharide molar ratio of approximately 2/1/1.

The structure of such a polysaccharide is explained in detail in the article by H. Rougeaux et al., published in *Carbohydrate Research*, 1999, 322, 40–45. It may be used in its native form or in a derived chemical form, the polysaccharide being, for example, functionalized with sulfate groups.

The polysaccharide used in the invention may be in a dry form, i.e. in a cottony, fibrous or pulverulent form, depending on the final treatment to which it is subjected (grinding makes it possible to obtain a powder, lyophilization results in a polymer with a cottony appearance, and drying makes it possible to obtain fibers). The polysaccharide used in the invention may also be in a hydrated form, for example in the form of a hydrogel. It might also be possible to envisage using such a polysaccharide in the form of a membrane or of a solid three-dimensional alveolate structure.

As a variant, the polysaccharide used in the invention may be combined with an osteoconductive and/or osteoinductive material.

Such an osteoconductive material may in particular be selected from the group consisting of deproteinized and/or ceramized bone, such as the bones marketed respectively by the laboratory S.P.A.D. (Quetigny, France) and the company OSTE (Clermont-Ferrand, France) under the names Laddec® and Lubboc®, synthetic or natural calcium phosphates (such as β-form tricalcium phosphate, biphasic calcium phosphate, hydroxyapatite or corals), biovitroceramics and bioglasses (for example Bioglas® and Perioglas® marketed by the laboratory PHARMADENT (Levallois-Perret, France).

As regards the osteoinductive material which can be combined with the polysaccharide used in the invention, it may be a hormone or a growth factor, in particular BMPs. Combining said polysaccharide with an osteoinductive material makes it possible to increase the rate of repair, for example by supplying BMPs directly to the damaged site. The polysaccharide used in the invention, excreted by the *Vibrio diabolicus* species, serves as a support for the osteoinductive material and protects it from enzymatic degradation.

A subject of the invention is also a bone reconstruction biomaterial, characterized in that it comprises a polysaccharide excreted by the *Vibrio diabolicus* species whose the strain was deposited with the CNCM on Oct. 17, 1995, under the number I-1629, and also an osteoconductive and/or osteoinductive material, for example such as those described above.

Besides the above arrangements, the invention also comprises other arrangements which will emerge from the following description, which makes reference to examples of use of the polysaccharide produced by the *Vibrio diabolicus* bacterium in bone repair. It should be clearly understood, however, that these examples are given only by way of illustration of the subject of the invention, of which they in no way constitute a limitation.

EXAMPLE 1

Obtaining an Exopolysaccharide Produced by the *Vibrio Diabolicus* Bacterium a) *Vibrio diabolicus* cultures The strain HE 800 is cultured on 2216E medium (Oppenheimer, *J. Mar. Res.*, 1952, 11, 10–18) enriched with glucose (40 g/l). The production is carried out at 30° C. and at pH 7.4 in a 2 liter fermenter containing 1 liter of the glucose-containing 2216E medium, as described by P. Vincent et al. in *Appl. Environ. Microbiol.*, 1994, 60, 4134–4141. After culturing for approximately 48 hours, the culture medium has a viscosity of the order of 100 centipoises at 60 rpm.

b) Purification of the exopolysaccharide

After 50/50 dilution with distilled water, the bacteria are separated from the culture medium by centrifugation at 20 000 g for 2 hours. Sodium chloride is then added to the diluted solution in such as way as to achieve a concentration of this salt of 20 g/l. The solution is maintained at ambient temperature and the polysaccharide is precipitated from the supernatant using pure ethanol at 4° C. The polysaccharide is recovered and is then subjected to several washes with ethanol/water with increasing proportions of ethanol (70/30, 80/20, 90/10 and 100/0 by volume), in accordance with the method described by F. Talmont et al. (*Food Hydrocolloids*, 1991, 5, 171–172) or by P. Vincent et al. (ibid).

The polymer obtained is dried at 30° C. and conserved at ambient temperature. Approximately 4.5 g of purified polysaccharide per liter of culture were thus obtained.

EXAMPLE 2

Use of the Exopolysaccharide Produced by the *Vibrio Diabolicus* Bacterium, in vivo, as Bone Filling Biomaterial a) Protocol 10 6- to 7-week-old male Wistar rats weighing 275 to 299 g are used. The rats are subjected to parenteral anesthesia using Nesdonal® (0.1 ml/100 g, Specia Rhône Poulenc Rorer, Montrouge, France), after intramuscular sedation with Ketamine (100 mg/kg) in the Imalgene® formulation (Mérial, Lyons, France) and subcutaneous premedication with Robinul® (0.01 mg/kg, Vetoquinol, Lure, France) half an hour before anesthesia.

Burr holes 5 mm in diameter are made in the calvaria of the rats, in both parietal lobes, on either side of the midsagittal suture, according to the protocol described by P. Cuevas et al. (*Surg. Neurol.*, 1997, 47, 242–6) or by C. Bosch et al. (*Cleft Palate Cranofacial Journal*, 1995, 32(4), 311–317): the animals' cranium is shaved using clippers and then a two-blade razor. Pre- and postoperative disinfection of the surgical site is performed with 10% dermal Betadine (Asta Medica, Merignac, France). A median incision is made over approximately 20 mm and the cutaneous tissues are bent back, as is the periosteum. The burr holes, under irrigation with physiological saline, are made with ballshaped diamond cutters, reference 801.104.014, 1.4 mm in diameter (Komet, France). An orifice is made on the right parietal, and another on the left parietal, taking care not to damage the dura mater.

Once the two burr holes have been made, the exopolysaccharide obtained in example 1 (between 1 and 2 mg) is positioned, in its native form (dry structure with an appearance similar to cotton), in the cavity made in the right parietal, whereas the second cavity is not filled and will be used as a control. The periosteum is sutured using a Vicryl® 3.0 resorbable thread (Johnson & Johnson Intl., Brussels, Belgium) and the sutures for the cutaneous layers are made of a nonresorbable material.

The animals are then placed in cages, and sacrificed by injection of pentobarbital (Doléthal®, Vétoquinol, Lure, France) after two weeks. The calvaria are removed, fixed with formaldehyde and demineralized before being studied histologically.

b) Results

The polysaccharide excreted by the *Vibrio diabolicus* bacterium enables bone repair by filling, for all the animals tested, the cavities made in the calvaria of the rats. From the histological point of view, no inflammatory reactions are noted, the polysaccharide used is no longer detectable and the bone newly formed in two weeks is perfectly structured: the collagen fibers are oriented, the osteoblasts cover the bone surfaces, and osteocytes are present. This bone is histologically normal. It is also observed that neovascularization is very marked and that the cutaneous connective tissue has not proliferated in an uncontrolled manner. In addition, the cutaneous scarring is of an excellent quality, with no proliferative phenomenon.

c) Comparative experiments

The cicatrizing properties of the polysaccharide excreted by the *Vibrio diabolicus* bacterium were compared with three other polysaccharides, named A, B and C, in table I below.

Polysaccharide A is a high molecular weight (of the order of 1 million g/mol) fucan of Phaeophyceae.

Polysaccharide B is produced by the strain of *Alteromonas macleodii* subsp. *fijiensis* named ST 716, described by Raguenes et al. in *Applied and Environmental Microbiology*, 1996, 62(1), 67–73 and deposited by IFREMER, according to the Treaty of Budapest, on Oct. 17, 1995, with the CNCM (Collection nationale de Cultures de Microorganismes [National collection of cultures of microorganisms]) held by the Pasteur Institute, 28 rue du Docteur Roux, in Paris, under the number I-1627. The production of his polysaccharide in a purified form is described in the PCT International publication published under the number WO 99/67411.

As described in the PCT International publication published under the number WO 99/67411, polysaccharide B consists of glucose, galactose, glucuronic acid, galacturonic acid and pyruvate mannose, these various constituents being respectively represented in the molar ratios 1/1/1/2/1, and associated in a hexasaccharide repeat unit in which three saccharide residues form a main chain, the branching point of which consists of a galacturonic acid residue. Grafted onto the latter is a side chain which terminates with a mannose residue with a pyruvate at position 4 and at position 6.

A polysaccharide B consists of the basic hexasaccharide unit corresponding to the formula (I) below:

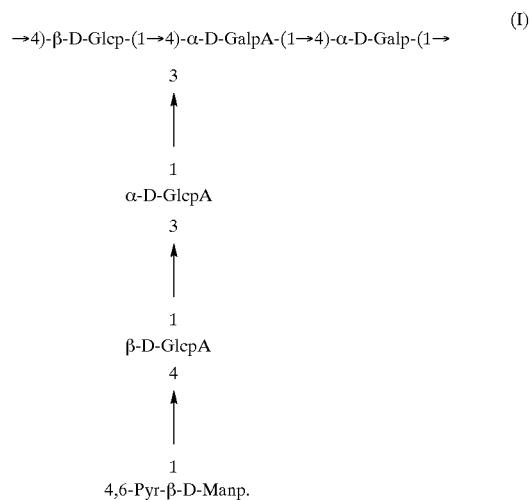

Polysaccharide C is produced by precipitation, using 40% (by volume) ethanol, from culture supernatants of the *Pseudoalteromonas* strain named HYD 721, as described in the article by H. Rougeaux et al. published in *Carbohydrate Research*, 1999, 315, 273–285. The basic octasaccharide unit of this polysaccharide corresponds to the formula (II) below:

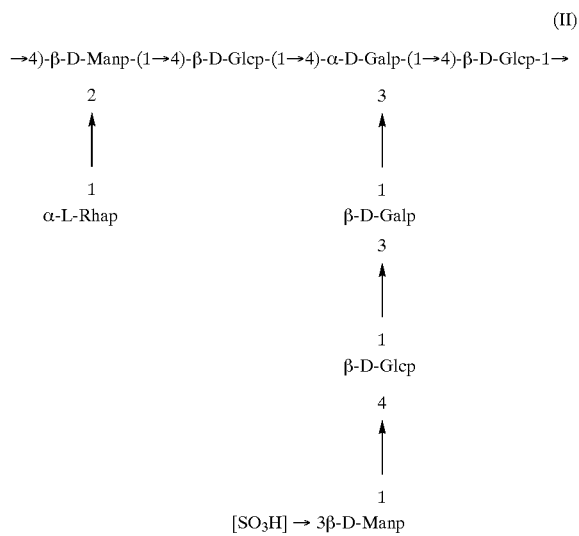

To assess the cicatrizing activity of the three polysaccharides A, B and C and the polysaccharide excreted by the *Vibrio diabolicus* bacterium, a surgical protocol identical to that described in point a) above was used. The results were quantified by comparing the surface of the newly formed bone relative to that of orifices made initially, this comparison being interpreted in terms of percentage filling of the orifices. Table I below therefore gives the number of animals for which zero (0%), slight (up to 25%), average (up to 50%), extensive (up to 99%) or complete (100%) filling of the orifices is observed.

TABLE I

| Polymer | Total number of animals | Filling of orifices: | | | | |
|---|---|---|---|---|---|---|
| | | zero | slight | average | extensive | complete |
| A | 3 | 3 | 0 | 0 | 0 | 0 |
| B | 10 | 0 | 2 | 6 | 2 | 0 |
| C | 5 | 4 | 1 | 0 | 0 | 0 |
| polysaccharide excreted by the *Vibrio diabolicus* species | 8 | 0 | 0 | 0 | 1 | 7 |

It appears therefore that, among the polysaccharides tested, only the polysaccharide excreted by the *Vibrio diabolicus* bacterium allows complete repair of orifices formed in the rat calvaria.

d) Conclusion

Thus, the polysaccharide excreted by the *Vibrio diabolicus* bacterium makes it possible, reproducibly and in approximately two weeks, to fill critical size bone defects (5 mm in diameter) in rat calvaria. Tests on 8 mm cavities and with a 4-week time period also allowed complete repair of a good quality. The critical lesions reconstitute ad-integrum without the uncontrolled effects observed with the use of BMPs. The polysaccharide used does not cause any inflammatory reaction and is completely resorbed by the surrounding tissues. The polysaccharide excreted by the *Vibrio diabolicus* bacterium therefore constitutes a material which potentiates bone repair. Its action is due to its original physicochemical characteristics. It also induces 80% repair of the control orifice, over the same period of time.

The invention claimed is:

1. A bone reconstruction biomaterial, comprising a polysaccharide excreted by the *Vibrio diabolicus* species having cicatrizing activity, and at least one of an osteoconductive or osteoinductive filler material.

2. A bone endoprosthesis at least partially coated with a polysaccharide excreted by the *Vibrio diabolicus* species having cicatrizing activity.

3. A method for cicatrizing bone comprising:
   administering to a subject in need thereof a polysaccharide excreted by the *Vibrio diabolicus* species to said bone in an amount effective for cicatrizing the bone.

4. The method of claim 3, wherein the polysaccharide is administered in an amount effective for repairing the bone.

5. The method of claim 3, further comprising
   coating a bone endoprosthesis with the polysaccharide.

6. The method of claim 3, further comprising
   administering an osteoconductive filling material to bone.

7. The method of claim 3, wherein the polysaccharide is obtained by precipitation with ethanol from culture supernatants of the *Vibrio diabolicus* species.

8. The method of claim 3, wherein the polysaccharide does not comprise any neutral polysaccharides, has an acid saccharide content of 50% by weight, has an osamine content of 50% by weight, and has a glucoronic acid/N-acetylgalactosamine/N-acetylglucosamine monosaccharide molar ratio of 2/1/1.

9. The method of claim 3, wherein the polysaccharide is present in a composition at least one of an osteoconductive or osteoinductive filler material.

10. The methos of claim 9, comprising administering a composition comprising an osteoconductive material selected from the group consisting of a deproteinized bone, deceramized bolne, a synthetic calcium phosphate, a natural calcium phophate, biovitroceramic and a bioglass.

* * * * *